United States Patent [19]

Geyer et al.

[11] Patent Number: 5,310,960
[45] Date of Patent: * May 10, 1994

[54] LOW TEMPERATURE PROCESS FOR PREPARING NEOMORPHIC IBUPROFEN

[75] Inventors: Robert P. Geyer, Brookline, Mass.; Vinod V. Tuliani, Media, Pa.

[73] Assignee: Affinity Biotech, Inc., Boothwyn, Pa.

[ * ] Notice: The portion of the term of this patent subsequent to May 10, 2011 has been disclaimed.

[21] Appl. No.: 86,922

[22] Filed: Jul. 2, 1993

[51] Int. Cl.$^5$ ............................................. C07L 53/134
[52] U.S. Cl. ..................................................... 562/496
[58] Field of Search ........................................ 562/496

[56] References Cited

U.S. PATENT DOCUMENTS

| | | | |
|---|---|---|---|
| 3,625,711 | 12/1971 | Eisenstadt | 99/141 A |
| 4,049,699 | 9/1977 | Sinkula | 560/105 |
| 4,049,700 | 9/1977 | Sinkula | 560/105 |
| 4,361,580 | 11/1982 | Peck et al. | 424/287 |
| 4,726,966 | 2/1988 | Kawashima et al. | 427/213.36 |
| 4,835,186 | 5/1989 | Reuter et al. | 514/570 |
| 4,835,188 | 5/1989 | Ho et al. | 514/570 |
| 4,916,161 | 4/1990 | Patell | 514/570 |

OTHER PUBLICATIONS

Vinod Labhasetwart, et al., *Studies on Some Crystalline Forms of Ibuprofen*, Drug Development and Industrial Pharmacy, 19(6), 631–641 (1993).

*Primary Examiner*—Paul J. Killos
*Attorney, Agent, or Firm*—Woodcock Washburn Kurtz Mackiewicz & Norris

[57] ABSTRACT

A novel neomorphic form of ibuprofen and processes for its preparation are provided. The neomorphic ibuprofen is characterized by having a distinctively less bitter and acidic taste commonly associated with conventional ibuprofen and which causes less burning sensation upon swallowing. The neomorphic form of ibuprofen is an amorphous ibuprofen and is prepared by resolidifying supercooled ibuprofen at a process temperature below 0° C.

16 Claims, 1 Drawing Sheet

LOW TEMPERATURE PROCESS FOR PREPARING NEOMORPHIC IBUPROFEN

FIELD OF THE INVENTION

The present invention relates to processes for the preparation of a novel form of ibuprofen characterized by having a distinctively less bitter and acidic taste that is normally associated with conventional ibuprofen and which exhibits less of a burning sensation upon swallowing, and also to the neomorphic ibuprofen prepared by those processes.

BACKGROUND OF THE INVENTION

Ibuprofen is one of the most popular non-steroidal anti-inflammatory drugs available today. Conventional ibuprofen is known to have a distinctly bitter, acidic, foul taste and to cause a burning sensation in the mouth and throat upon oral administration. Therefore, various attempts have been made to mask the taste of ibuprofen, the most common being to coat the ibuprofen in a tablet form for oral administration without chewing, usually accompanied with liquids to aid the swallowing, thus hiding the unpleasant taste of the free acid.

Unfortunately, a substantial portion of the population cannot swallow a tablet form of ibuprofen and this is particularly true in the young and aged. These individuals commonly take the ibuprofen in a liquid form, however the foul taste of the ibuprofen in liquid form will most likely preclude compliance among these individuals.

Various attempts have been made to mask the taste of ibuprofen. The most common attempts incorporate the use of taste-masking agents with the ibuprofen, accompanied in many cases by costly production procedures. Examples of these prior efforts include admixing hydroxypropyl methylcellulose phthalate with the ibuprofen in a wet granulation process as shown in U.S. Pat. No. 4,916,161; spray drying a dispersion of ibuprofen, ethyl cellulose, and a plasticizer as shown in U.S. Pat. No. 4,835,188; dissolving ibuprofen with acrylic acid resin in an organic solvent and water to provide a granulated ibuprofen as shown in U.S. Pat. No. 4,726,966; and spray drying ibuprofen in a suspension of colloidal silica, alcohol, and cellulose acetate as shown in U.S. Pat. No. 4,835,186. Various attempts have also been made to alter the chemical structure of ibuprofen to a form that has a less objectionable taste as shown in U.S. Pat. Nos. 4,049,699 and 4,361,580, however the utility of these forms remains to be determined.

There still exists a need in the art to develop a taste-masked form of ibuprofen which can be prepared easily and does not require the additional blending of specific amounts of certain taste-masking agents.

SUMMARY OF THE INVENTION

The present invention provides an improved tasting neomorphic form of ibuprofen and methods for its preparation. This new form of ibuprofen is characterized by having an amorphous structure. By "amorphous" is meant that the neomorphic form of ibuprofen has no defined crystalline structure characteristic of conventional ibuprofen. This characteristic is easily determined by visual inspection using microscopic means and by birefringence testing. The neomorphic form exhibits substantially no birefringence while the conventional crystalline form exhibits birefringence.

The neomorphic ibuprofen produced by the processes of the present invention is generally characterized as being a bulky material having a flaky appearance on the top of the material. The neomorphic ibuprofen, when broken into smaller particles, is seen to have an amorphous, non-crystalline structure. The neomorphic ibuprofen particles are thus distinct morphologically from conventional ibuprofen which is characterized by having a rod-like crystalline structure, being usually about 100 microns in length and up to about 20 microns in width, and thus having an averaged particle size, average of the length and width of the particles, of less than about 100 microns, although this can vary depending upon the particular manufacturer. The conventional crystalline ibuprofen can be characterized by its ability to exhibit birefringence.

The neomorphic ibuprofen can be prepared by various methods. Common to the methods is the alteration of the normal resolidification of ibuprofen from an ibuprofen melt which resolidification ordinarily yields crystalline ibuprofen. The methods are performed by first providing ibuprofen in a supercooled state. Typically, the ibuprofen is heated past its melting point resulting in a molten ibuprofen. This molten ibuprofen is then cooled below its melting point while maintaining the molten condition, thus achieving a supercooled ibuprofen state.

The resolidification of the supercooled ibuprofen is then accomplished by altering the conditions to inhibit the normal recrystallization of the ibuprofen. One such method is to allow the resoldification to occur at relatively low process temperatures of from below 0° C., preferably below about −10° C., more preferably below −20° C. The lower temperature limit is dependent upon processing factors, however temperatures as low as about −70° C., preferably −60° C., and more preferably −40° C. are practicable. The resolidification process is then allowed to proceed at these process temperatures.

Another method for resolidifying the ibuprofen into the improved tasting neomorphic ibuprofen requires that some form of energy, preferably in the form of kinetic energy, also be imparted into the supercooled ibuprofen that is maintained at the process temperature. A further method for resolidifying to the neomorphic form is to seed the supercooled ibuprofen with neomorphic ibuprofen. The amorphous ibuprofen is then recovered.

DETAILED DESCRIPTION OF THE INVENTION

Figure 1:
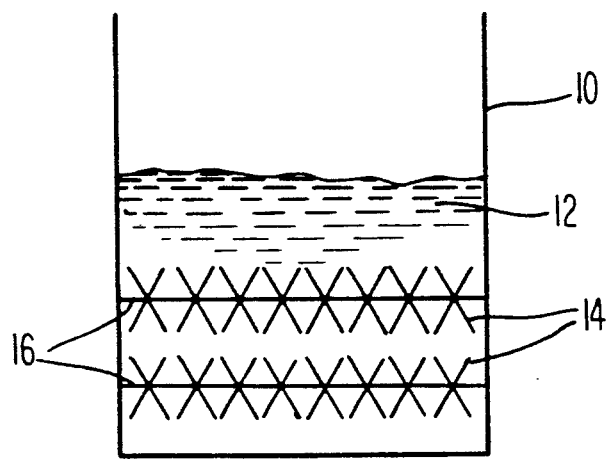
FIG. 1 is a cut-away view of a vessel in which the methods of the present invention can be practiced.

The present invention relates to a neomorphic form of the non-steroidal anti-inflammatory drug (NSAID) ibuprofen and preparatory methods for making the same. Conventional ibuprofen is characterized by its bitter taste upon mastication and burning sensation upon swallowing. The neomorphic form of ibuprofen of the present invention is characterized by having a bland or neutral taste and also a greatly reduced burning sensation felt upon the back of the throat upon swallowing of the drug. Thus the neomorphic form is ideally suited for administration of ibuprofen in any format, especially in a format other than in a taste-coated tablet that is to be swallowed without contact of the drug with the mouth or throat. Such administration forms include powders or tablets that can be chewed, liquid suspensions for drinking, or in some form that allows for the contacting of the ibuprofen with the mouth or throat.

Conventional ibuprofen, as used herein, refers to the chemical compound that has been chemically named ±2-(p-isobutylphenyl)propionic acid, 2-(4-isobutylphenyl)propionic acid, p-(iso-butyl)hydrotropic acid, and α-methyl-α-(p-isobutylphenyl)acetic acid, either as a racemic mixture or as either of its + or − isomers.

The present neomorphic form of ibuprofen is chemically similar to the conventional form of ibuprofen, but is different with respect to its physical characteristics and taste characteristics.

The neomorphic ibuprofen of the present invention can be produced in a wide variety of ways employing common physical and chemical characteristics of the ibuprofen. The production process takes advantage of the supercooled state of ibuprofen and the ability of the ibuprofen to resolidify under conditions that inhibit recrystallization.

The neomorphic ibuprofen of the present invention is prepared using a relatively low temperature resolidification process. The ibuprofen is heated above its melting point of about 74°–77° C., so the heating is preferably above about 75° C., more preferably from about 75°–90° C., resulting in a molten ibuprofen. This molten ibuprofen is then cooled to below its melting point to a process temperature of at least below 0° C., preferably below about 10° C., more preferably below −20° C. while maintaining the supercooled state. The lower limit for the process temperature is generally a function of the processing capabilities and is generally as low as about −70° C., preferably as low as −60° C., and more preferably −40° C. Therefore, the process temperature can be conveniently set at about −70° C. to 0° C., preferably −60° C. to −10° C., more preferably −40° C. to −20° C. The supercooled ibuprofen is a highly viscous liquid at these process temperatures. Preferably, agitation is minimized during the cooling of the molten ibuprofen to the supercooled state and to the process temperature to minimize any premature resolidification into the crystalline state.

The molten ibuprofen is then allowed to resolidify at the process temperature to the neomorphic form. The low process temperature inhibits the recrystallization of the ibuprofen to its normal crystalline form. The resolidification into the neomorphic ibuprofen can be promoted by stirring the supercooled ibuprofen. The neomorphic form of the ibuprofen is then recovered. This process yields the neomorphic form of ibuprofen in high yields of at least about 50 weight percent, preferably at least 70 weight percent, more preferably at least 90 weight percent, and most preferably at least 95 weight percent.

A further embodiment of the present invention is the preparation of the neomorphic ibuprofen at the above stated process temperatures along with the application of kinetic energy to the supercooled ibuprofen. In this method, upon cooling the supercooled ibuprofen to the process temperature, kinetic energy is imparted to the supercooled ibuprofen for a time sufficient to yield the neomorphic ibuprofen. Yields similar to those previously stated can be achieved with this process. The application of the kinetic energy reduces the time for the solidification of the supercooled ibuprofen into the neomorphic state.

The type of kinetic energy imparted into the supercooled ibuprofen will be dependent upon the type of processing system used to handle the manufacture. The kinetic energy can be in the form of a mechanical force directed at the vessel in which the supercooled ibuprofen is resolidified. The kinetic energy is applied to the supercooled ibuprofen for a time and intensity sufficient to cause resolidification into the neomorphic form. The processes for preparing the neomorphic ibuprofen using the application of kinetic energy are more fully set forth in a co-pending application entitled "Neomorphic Ibuprofen" in the name of the inventors of this application, application Ser. No. 087.573 filed Jul. 2, 1993. That application is incorporated herein in its entirety by reference.

Manufacture of the neomorphic ibuprofen in a batchwise manner can be accomplished by containing the supercooled ibuprofen in an appropriate vessel. Preferred vessels include plastic vessels that have a surface which favors the production of the neomorphic ibuprofen. If kinetic energy is used, it can then take the form of, for example, physically striking the vessel walls or vigorously stirring or striking the supercooled ibuprofen for a time and intensity sufficient to form the neomorphic ibuprofen. The vessel can be equipped with "seeding surfaces" which can take the form of any type of exposed surface inside the vessel upon which the supercooled ibuprofen can resolidify. As shown in FIG. 1, the vessel 10 containing the supercooled ibuprofen 12 can contain seeding surfaces 14, shown here as rod-like protrusions supported by bars 16.

The resolidification of the supercooled ibuprofen can also be enhanced by the "seeding" of the supercooled ibuprofen with the neomorphic ibuprofen. In this process, the supercooled ibuprofen is cooled to the process temperature and then an amount of neomorphic ibuprofen is added to the supercooled ibuprofen. Resolidification occurs either with or without application of stirring or kinetic energy.

The neomorphic ibuprofen can be described by its distinguishing physical features in relation to conventional ibuprofen. The conventional ibuprofen is characterized by its crystalline structure, while the neomorphic ibuprofen has an amorphous structure.

The amorphous ibuprofen exhibits no birefringence and is substantially colorless when viewed through partially or completely crossed polarized lenses. Conventional ibuprofen exhibits birefringence and reflects various colors when viewed through crossed polarizers. Generally, the neomorphic ibuprofen is chemically similar to conventional ibuprofen.

The neomorphic form of ibuprofen of the present invention can be masticated and swallowed in its unaltered form without the bitter taste and burning sensation caused by conventional ibuprofen. The neomorphic form can therefore be administered without the need for taste-masking or flavor enhancing additives or agents, however such components can be admixed with the neomorphic ibuprofen.

The neomorphic ibuprofen can be presented for administration with or without the above mentioned additives. Lubricants such as magnesium stearate, talc, calcium stearate, stearic acid, and hydrogenated vegetable oils, and flow control agents such as microcrystalline cellulose, microcrystalline dextrose, amylose, and polyvinylpyrrolidone can be used. The neomorphic ibuprofen can also be prepared as a liquid suspension or dispersion.

The dosage to effect the desired therapeutic result, "therapeutically effective amount", for this form of ibuprofen can be readily determined by those skilled in the art. Generally, ranges from about 100 mg to about 800 mg per dosage, which can be repeated about every 4 to 6 hours should provide acceptable responses. The various embodiments of the present invention are further described by the following nonlimiting examples.

EXAMPLE 1

Approximately one gram ibuprofen (BHC Corporation, Corpus Christi, TX) was placed in the bottom of a tall glass vial (height approx. 4.25 inches) while avoiding contact of the ibuprofen with the walls of the vial. The vial was then capped and heated in a water bath at around 88° C. to 91° C.

The vial was allowed to float in the water bath without touching the hot base of the bath, so that the material within would not be exposed to extremely high temperatures. The vial remained in this environment until all the ibuprofen melted. Once this had occurred, the vial was placed in a freezer at −20° C. Spontaneous solidification into a few opaque particles was seen to occur in time. The number of solidified particles was found to increase with time. Eventually, all the material was seen to have solidified. The vial and its contents were allowed to remain in that environment for 24 to 48 hours without being disturbed.

Some material was taken from the solidified mass and observed under a microscope. Under crossed polarized filters, it was seen to be dull and to have very little birefringence. Some material on the slide was gently crushed with a spatula. The crushed particles were also seen to have very little birefringence. The particles were found to have no bad taste or burning sensation on the tongue, throat and lips even upon chewing the particles.

EXAMPLE 2

The same procedure as in Example 1 was carried out through the melting stage. The vial was then placed in a glycerol bath maintained at −20° C., and the vial was swirled to mix the molten ibuprofen inside, while the ibuprofen viscosity was low. The viscosity was seen to increase as the temperature of the molten ibuprofen decreased. The vial was allowed to rest in the chilled glycerol bath for about two hours and was then placed in the freezer at −20° C. The subsequent procedure and testing of the material was performed in the same way as in Example 1. Upon testing the produced material under the microscope, it was found to comprise mainly non-birefringent particles.

EXAMPLE 3

The procedure was the same as in Example 1, except that, after melting and chilling, the highly viscous fluid ibuprofen was stirred. The stirring rod used was made of glass and its temperature was also at −20° C. because it had been maintained in the freezer, in order to have it at the same temperature as the bulk of the material. The material was found to solidify much faster than in Example 1. Upon testing the produced material under the microscope, it was found to comprise mainly non-birefringent particles.

EXAMPLE 4

After the melting and chilling as described in Example 1, the chilled material was seeded with some preformed resolidified neomorphic ibuprofen made in accordance with Example 1. The seeding was performed by placing 2-3 particles of neomorphic ibuprofen onto the surface of the bulk ibuprofen after melting and chilling the bulk ibuprofen. Relative to Example 1, the resolidification of the bulk into particles of the neomorphic form was found to proceed at a faster rate.

What is claimed is:

1. A process for preparing neomorphic ibuprofen having a bland taste and an amorphous structure, comprising:
    (a) providing molten ibuprofen in a supercooled state at a process temperature below 0° C.;
    (b) resolidifying the supercooled ibuprofen into a solid amorphous ibuprofen; and
    (c) recovering the solid amorphous ibuprofen.

2. The process of claim 1 wherein the amorphous ibuprofen exhibits no birefringence.

3. The process of claim 1 wherein the process temperature is below about −10° C.

4. The process of claim 3 further comprising adding amorphous ibuprofen to the supercooled ibuprofen.

5. The process of claim 1 wherein the resolidification is continued for a period of time to convert at least 70 percent by weight of the supercooled ibuprofen into solid amorphous ibuprofen.

6. The process of claim 1 wherein the process temperature is from about −70° C. to 0° C.

7. The process of claim 1 wherein the amorphous ibuprofen exhibits no birefringence.

8. The process of claim 1 further comprising adding amorphous ibuprofen to the supercooled ibuprofen.

9. The process of claim 6 further comprising providing the supercooled ibuprofen in a vessel wherein the vessel comprises seeding surfaces, and the method further comprises resolidifying the ibuprofen on said surfaces.

10. The process of claim 1 wherein the process temperature is from about −70° C. to −10° C.

11. The process of claim 10 wherein the amorphous ibuprofen exhibits no birefringence.

12. The process of claim 10 further comprising adding amorphous ibuprofen to the supercooled ibuprofen.

13. The process of claim 11 wherein the resolidification is continued for a period of time to convert at least 70 percent by weight of the supercooled ibuprofen into solid amorphous ibuprofen.

14. A process for preparing neomorphic ibuprofen having a bland taste and an amorphous structure, comprising:
    (a) providing molten ibuprofen in a supercooled state at a process temperature of below about −10° C.;
    (b) resolidifying the supercooled ibuprofen into a solid amorphous ibuprofen, wherein at least about 50 percent by weight of the supercooled ibuprofen is solidified into said amorphous ibuprofen; and
    (c) recovering the solid amorphous ibuprofen.

15. The process of claim 14 further comprising adding amorphous ibuprofen to the supercooled ibuprofen.

16. The process of claim 14 wherein the amorphous ibuprofen exhibits no birefringence.

* * * * *